United States Patent [19]

Nielsen

[11] Patent Number: 5,723,796

[45] Date of Patent: Mar. 3, 1998

[54] ATOMIZED FLUX APPLICATION TO SIMULATE SOLDERING

[75] Inventor: Clifford B. Nielsen, Milpitas, Calif.

[73] Assignee: Cypress Semiconductor Corp., San Jose, Calif.

[21] Appl. No.: 866,974

[22] Filed: Jun. 2, 1997

Related U.S. Application Data

[63] Continuation of Ser. No. 568,192, Dec. 6, 1995, abandoned.

[51] Int. Cl.$^6$ .................................................. G01M 19/00
[52] U.S. Cl. .................................................. 73/865.6
[58] Field of Search ........................ 73/865.8, 865.6, 73/865.3

[56] References Cited

U.S. PATENT DOCUMENTS

| | | |
|---|---|---|
| 4,731,154 | 3/1988 | Hausman-Hazlitt et al. . |
| 4,807,483 | 2/1989 | Wright et al. ............... 73/865.3 |
| 5,195,384 | 3/1993 | Duesler, Jr. et al. ......... 173/865.6 |
| 5,310,574 | 5/1994 | Holtmann ..................... 427/58 |
| 5,318,361 | 6/1994 | Chase et al. ................. 73/865.6 |
| 5,328,085 | 7/1994 | Stoops et al. ................. 228/33 |
| 5,368,219 | 11/1994 | Hogan et al. ................. 228/33 |
| 5,443,660 | 8/1995 | Gao et al. . |

*Primary Examiner*—Robert Raevis
*Attorney, Agent, or Firm*—Blakely Sokoloff Taylor & Zafman LLP

[57] ABSTRACT

The present invention describes a method for testing an electronic part which may be an integrated circuit by using an air brush spray gun to apply an atomized flux coating to the part. The purpose of the method is to simulate soldering and is used on only a sample of parts as part of a reliability procedure before subjecting the part to an additional stress test or before actually soldering the part. The method comprises the steps of: spraying each part with an atomized flux coating; heating each part to simulate a soldering process; and removing each part from a heat source.

14 Claims, 3 Drawing Sheets

ATOMIZED FLUX APPLICATION TO SIMULATE SOLDERING

This is a continuation of application Ser. No. 08/568,192 filed Dec. 6, 1995, now abandoned.

BACKGROUND OF THE INVENTION

The present invention relates generally to testing of integrated circuits, and more particularly to a method for testing an electronic part by applying a flux coating to the part to simulate a soldering process.

The functionality and reliability of an electronic part is often tested as part of a known procedure during semiconductor integrated circuit fabrication. The functionality tests determine whether an electronic part will operate as expected, for example, whether it will operate within certain power supply voltages. For example, if an electronic part is expected to function with power supply voltages of 0V and 5V, then it should also be able to tolerate variations from these voltages. The reliability tests determine whether an electronic part will still perform as expected even after many years of use.

As part of its reliability procedures, a semiconductor integrated circuit fabrication company may take a certain number of sampled electronic parts, each part comprising a packaged integrated circuit, and test those parts by simulating the soldering process prior to actually soldering the part. The old method of simulating soldering required applying conventional liquid flux to a part, particularly the leads of a part, using a flux application dropper bottle. An operator would then put the part into a reflow oven for approximately three minutes. At the end of the three minutes, the part would be removed from the oven and allowed to cool, and the process repeated three times. In this manner, a soldering operation is simulated, and then conventional reliability and functional tests may be performed on this part which was exposed to a simulated soldering. Thus, the reliability and functionality of the part (and consequently the other parts not sampled for testing) may be determined.

The old method of using the flux application dropper bottle required the operator to adjust the drop application to the individual parts using finger pressure on the bottle. The operator would have to adjust the finger pressure depending on the size of the part. For instance, a small component part, such as a 16 pin Small Outline, J bend (SOJ) required extreme motor control, while a larger part, such as an 84 pin Plastic Leaded Chip Carrier (PLCC) had more pins and thus required the operator to maintain steady finger pressure for a longer period of time. In an ideal situation, the tip of the dispenser of the dropper bottle was close enough to "drag" a drop of liquid flux along the length of the side of the component part. Unfortunately, after applying the flux to a few parts, the tip was generally running in contact with the pins and the flow became uneven. The problem with the old method of applying flux is that it required the operator to have great eye-to-hand coordination combined with good and even control of finger pressure for flow control. Consequently, the operator would become tired quickly and low productivity resulted. Thus, what is needed is a method of uniformly and easily applying a liquid flux coating to an electronic part.

SUMMARY OF THE INVENTION

It is desirable to test an electronic part which may be a packaged integrated circuit by applying a flux coating to the part.

According to the preferred embodiment of the present invention, one method of testing a packaged integrated circuit which comprises a discrete component part is by spraying flux coating to the component part; heating the part to simulate soldering; and then removing the part from a heat source. In addition, not a single component part should touch another part during the heating process. In one embodiment of the invention, a method for applying an atomized flux coating includes the use of an air brush spray gun which uses very low pressure. A high pressure spray gun is not preferred because the spray from the gun may cause a part to move around. In yet another aspect of the invention, the atomized flux coating is allowed to fully cover each lead of a part evenly before putting the part in a reflow oven.

In one embodiment of the invention, an operator places an electronic part, such as a surface mount device (SMD), on a tray. The operator then sprays each of the parts with flux coating from an air brush spray gun. Then the parts are heated in a reflow oven to simulate the soldering process. Finally, the operator removes the parts from the reflow oven and allows the parts to cool. The operator, in one embodiment of the invention, may repeat the above preconditioning test at least once, before rinsing the flux coating off of the parts and then performing an additional stress test on the part. In another embodiment of the invention, the operator may simply send the part to an additional stress test after only performing the preconditioning test once.

In yet another embodiment of the invention, the operator may heat the parts in a reflow oven at a temperature range of approximately 183° C. for at least one minute, during which time a temperature of 210° C. must be reached for at least 10 seconds, before allowing the part to cool and then rinsing the flux coating off of the part. The operator may then send the part onto an additional (conventional) stress test. A temperature cycling test is one stress test that an operator may perform after the preconditioning test which simulates soldering. In the temperature cycling test, an operator will expose a component part to temperatures ranging from approximately –65° C. to approximately 155° C. The operator, in another embodiment of the invention, may forego the temperature cycling test or in addition to the temperature cycling test, then expose the part to a Highly Accelerated Stress Test (HAST). The HAST involves placing an electronic part that is electrically biased in a chamber, that has extreme humidity (approximately 85%), and that has a temperature of about 140° C. for many hours.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

DETAILED DESCRIPTION OF THE PRESENT INVENTION

A method of applying liquid flux to a discrete component part to simulate soldering is described. In the following description, numerous details are set forth, such as a surface mount device or a particular spray gun. It will be apparent, however, to one skilled in the art, that the present invention may be practiced without these specific details. For example, the electronic device or part may be discrete components (not an integrated circuit) or may be other conventional integrated circuit packages, such as a single in-line memory module (SIMM), dual in-line packages (DIPs), etc. In other instances, well-known structures and processes have not been set forth in detail in order to avoid obscuring the present invention.

Figure 1:
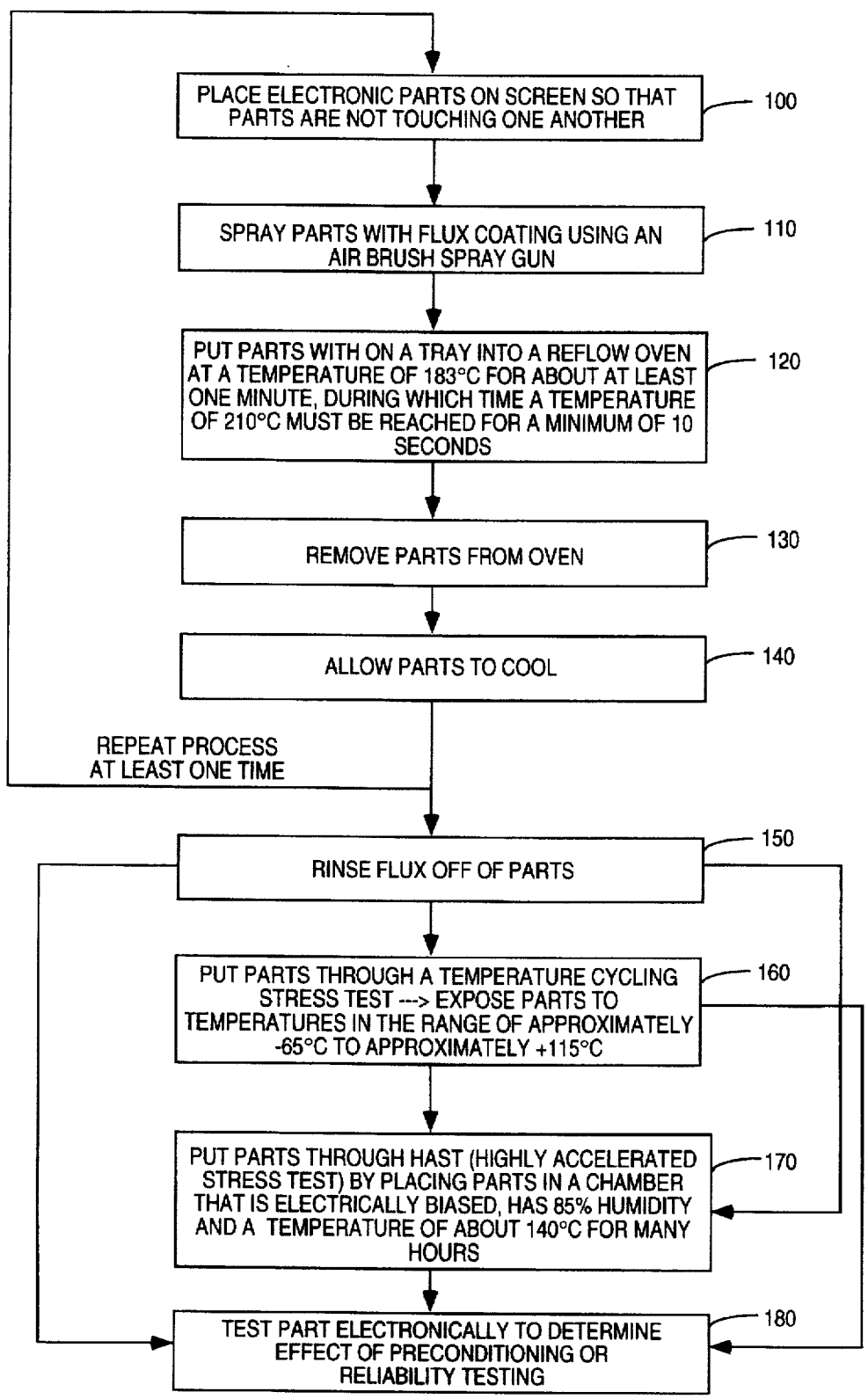
FIG. 1 illustrates a flow chart of the method of the present invention and two related stress tests.

FIG. 1 illustrates a flow chart of the method of the present invention and two related stress tests, the temperature cycling stress test and the Highly Accelerated Stress Test (HAST) which are not part of the present invention. According to the preferred embodiment of the invention, an operator places an electronic part (e.g., an integrated circuit (IC)) on a screen so that one part is not touching another part (see Block 100 of FIG. 1). A conventional liquid flux is introduced into the container 10 of a spray gun 8 (see FIG. 3). The operator then sprays the parts with conventional flux coating using the air brush spray gun (see Block 110 of FIG. 1) and places the parts on a tray into a reflow oven at a temperature range of approximately 183° C. to 210° C. for about at least one minute during which time a temperature of 210° C. should be reached for a minimum of ten seconds (see Block 120 of FIG. 1). The operator removes the parts from the oven (see Block 130 of FIG. 1) and allows the parts to cool (see Block 140 of FIG. 1). The operator may repeat the process at least one more time or three times which is the preferred embodiment. In another embodiment of the invention, the operator will rinse the flux off of the parts (see Block 150 of FIG. 1) and then put the parts through an additional stress test, such as a temperature cycling stress test (see Block 160 of FIG. 1) and/or HAST (Highly Accelerated Stress Test) (see Block 170 of FIG. 1). The part is then tested electronically to determine the effect of the reliability and functionality tests.

Figure 2:
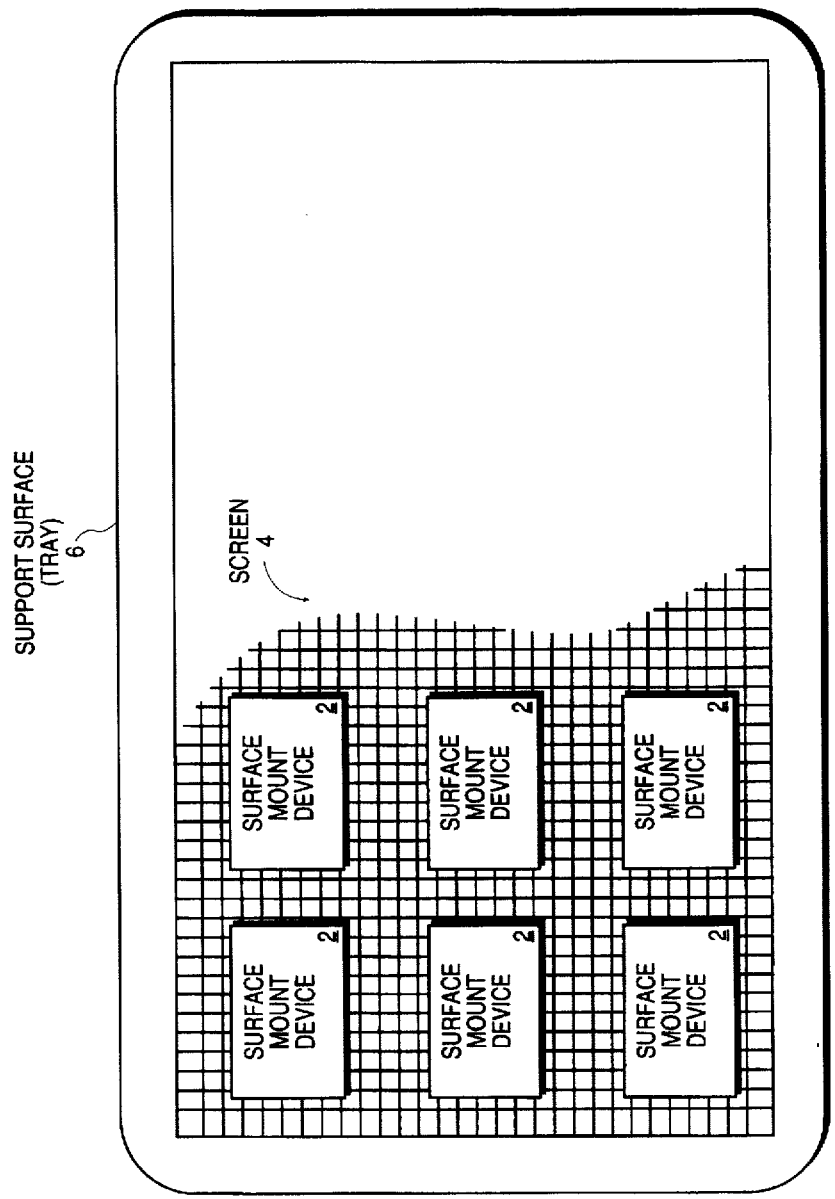
FIG. 2 illustrates how a component part, in particular a surface mount device (SMD), is placed on a screen which is on a tray.

FIG. 2 illustrates how a component part, in particular a surface mount device (SMD) 2, is placed on a screen 4 which is on a tray 6. A screen 4 is placed on the tray 6 so that after the part 2 has been sprayed with liquid flux, any excess liquid flux may be drained away from the surface of the part 2.

Figure 3:
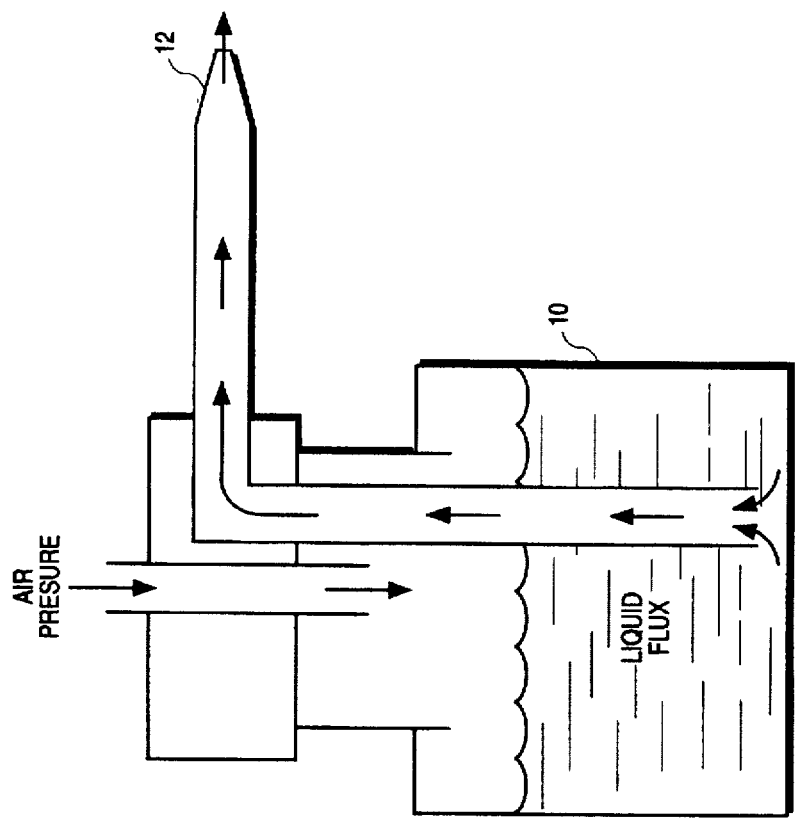
FIG. 3 is a schematic illustration of how an air brush spray gun works.

FIG. 3 is a schematic illustration of how an air brush spray gun 8 works. The air pressure causes the liquid flux which is placed inside container 10 of the spray gun 8 to leave the gun 8 through a nozzle 12. The liquid flux is atomized as it leaves the nozzle 12 which causes the liquid flux to be uniformly applied to the part. According to the preferred embodiment of the invention, the air brush spray gun employs very low pressure so as not to damage or move the part during the process of spraying the part with liquid flux to simulate soldering. In yet another embodiment, the air brush spray gun 8 is a conventional spray gun used for painting by artists. In one embodiment, a Badger 150 spray gun manufactured by Badger Air-Brush Co. which is located at 9128 W. Belmont Ave., Franklin Park, Ill. 60131 is used.

I claim:

1. A method for testing a packaged integrated circuit which comprises a discrete component part by applying an atomized flux coating to said discrete component part, said method comprising:

placing said part on a support surface;

spraying said part with said atomized flux coating from an air brush spray gun;

heating said part to simulate a soldering process;

removing said part from a heat source;

allowing said part to cool;

repeating all of the above steps at least once;

rinsing said flux coating off of said part; and testing said part electronically to determine the reliability and functionality of said part.

2. A method for applying a flux coating, as in claim 1, wherein said part is a surface mount device (SMD) part.

3. A method, as in claim 1, said method further comprising the step of:

performing an additional stress test on said part before testing said part electronically.

4. A method, as in claim 3, wherein said additional stress test is a temperature cycling test, said temperature cycling test comprising:

exposing said part to temperatures ranging from approximately –65° to approximately 155° C.

5. A method, as in claim 3, wherein said additional stress test is a Highly Accelerated Stress Test (HAST), said HAST comprises:

placing said part in a chamber that is electrically biased, with an extreme humidity (approximately 85%); and exposing said part to a temperature of approximately 140° C. for many hours.

6. A method for applying a flux coating, as in claim 1, wherein said part is a surface mount device (SMD) part.

7. A method for applying a flux coating, as in claim 1, wherein said placing of said part is such that no other part on said support surface touches said part.

8. A method for applying a flux coating, as in claim 1, wherein said air brush spray gun uses a very low pressure so that said part is not moved by said air brush spray gun.

9. A method for applying a flux coating, as in claim 1, wherein said heating occurs by placing said part in a reflow oven at a temperature range of 183° C.–210° C. for a predetermined amount of time.

10. A method, as in claim 1, wherein said spraying applies said atomized flux coating in a quick and even application onto said part.

11. A method, as in claim 1, wherein said flux coating is a water-soluble liquid flux.

12. A method for testing a packaged integrated circuit comprising the steps of:

spraying said integrated circuit with a flux coating;

heating said integrated circuit to simulate soldering; and testing said integrated circuit electronically to determine the reliability and functionality of said integrated circuit.

13. A method for testing a packaged integrated circuit as in claim 12 further comprising the step of removing said integrated circuit from a heat source prior to testing said integrated circuit.

14. A method of testing a packaged integrated circuit as in claim 12 further comprising the step of repeating said steps of spraying and heating at least once prior to said step of testing.

* * * * *